United States Patent [19]

Whitebook

[11] Patent Number: 5,354,323
[45] Date of Patent: Oct. 11, 1994

[54] OPTICAL HEATING SYSTEM

[75] Inventor: Mark E. Whitebook, Dana Point, Calif.

[73] Assignee: Premier Laser Systems, Inc., Irvine, Calif.

[21] Appl. No.: 997,554

[22] Filed: Dec. 28, 1992

Related U.S. Application Data

[63] Continuation-in-part of Ser. No. 963,470, Oct. 20, 1992, abandoned.

[51] Int. Cl.⁵ .............................................. A61N 5/06
[52] U.S. Cl. .................................... 607/89; 606/11; 606/12
[58] Field of Search ............... 128/395–398, 128/664–665, 303.1; 219/121 LZ, 121 LB; 606/2, 3, 10–12; 607/88–95

[56] References Cited

U.S. PATENT DOCUMENTS

| | | | |
|---|---|---|---|
| 3,995,623 | 12/1976 | Blake et al. | |
| 4,121,087 | 10/1978 | Malmuth et al. | 219/121 |
| 4,316,467 | 2/1982 | Muckerheide | |
| 4,632,125 | 12/1986 | Webler et al. | 128/692 |
| 4,644,948 | 2/1987 | Lang et al. | 128/395 X |
| 4,672,969 | 6/1987 | Dew | |
| 4,854,320 | 8/1989 | Dew et al. | |
| 4,887,606 | 12/1989 | Yock et al. | 128/662.05 |
| 4,901,734 | 2/1990 | Griffin et al. | 128/692 |
| 4,953,553 | 9/1990 | Tremulis | 128/637 |
| 4,953,929 | 9/1990 | Basista et al. | 350/96.2 |
| 5,002,051 | 3/1991 | Dew et al. | |
| 5,050,597 | 9/1991 | Daikuzono | 128/395 |
| 5,057,099 | 10/1991 | Rink | 606/12 |
| 5,140,984 | 8/1992 | Dew et al. | 128/395 |
| 5,219,345 | 6/1993 | Potter | 606/15 |

OTHER PUBLICATIONS

James H. Philip, Member, IEEE, Michael C. Long, Michael D. Quinn, Member, IEEE and Ronald S. Newbower, Member, IEEE; *Continuous Thermal Measurement of Cardiac Output*, IEEE Transactions on Biomedical Engineering, vol. BME-31, No. 5, May 1984.

*Primary Examiner*—Angela D. Sykes
*Attorney, Agent, or Firm*—Steven C. Stewart; James H. Beusse

[57] ABSTRACT

A laser heating system projects a beam of optical radiation on a region to be heated. A sensor detects changes in temperature of the region by sensing the black body radiation of the heated region. A control circuit then controls the intensity of the beam as a function of the sensed black body radiation. In another embodiment, the beam is moved among the region and the light intensity of the beam is dynamically controlled.

25 Claims, 1 Drawing Sheet

OPTICAL HEATING SYSTEM

This is a continuation-in-part of application Ser. No. 07/963,470, filed Oct. 20, 1992, now abandoned.

BACKGROUND OF THE INVENTION

This invention relates to optical heating systems and more particularly to a method and apparatus for controlling the temperature of a region of material when heating with optical radiation.

Optical radiation is commonly used in many medical and industrial applications. One example of an optical radiation technique is using a laser welding procedure to seal wounds. In a laser welding procedure, edges of a wound are placed adjacent or in close approximity to each other and then heated by radiation from a laser at a wavelength of about 1.3 microns (near infrared region). The laser radiation is fed through an optical fiber and then directed at the wound. The tissue at the wound is then heated for a time duration sufficient to permit the tissue to denature and seal but not long enough to scorch. Examples of this procedure are described in more detail in U.S. Pat. Nos. 4,672,969, 4,854,320, 5,002,051, and 5,140,984.

When using the aforementioned procedures, a surgeon would direct laser energy from an emitter (optical fiber end) onto the area of the tissue to be heated. A spacing device is used to maintain a predetermined distance between the laser emitter and the material to be heated. The surgeon then activates the laser and heats the wound for a fixed time. The laser is then deactivated and the laser emitter is pointed to a new spot where the procedure is repeated. Critical to this procedure is maintaining the predetermined distance between the laser emitter and the tissue to be heated, as well as maintaining a constant power, intensity, and duration of the laser radiation. By doing so, the tissue being heated will reach the desired end temperature critical to the welding process.

A drawback to the aforementioned technique is that if the laser emitter is moved while the tissue is being heated such that the laser emitter becomes too close to the tissue, the tissue may overheat. This overheating may cause tissue scorching or shrinking and result in both scarring and an inadequate weld. If the laser emitter moves too great a distance from the tissue, the desired end temperature at which tissue denatures may not be reached and the wound may not close.

Another concern in tissue welding is that not all optical fibers through which the laser radiation is propagated to the wound are alike. Some fibers have greater attenuation than other fibers. Thus, certain fibers generate a small focal spot where another fiber may generate a large focal spot. These variations may cause the wound to heat faster or slower than desired.

One solution to overcome the problem of inconsistent heating is to use a thermocouple or a temperature probe. The thermocouple is placed on the area to be heated and measures the temperature rise of the area it contacts. A drawback of the thermocouple is that it may obscure at least part of the spot being heated. Consequently, the thermocouple can act as a heat sink and can interfere in the welding process. Further, the thermocouple may only measure temperature of a small portion of the spot being heated. Consequently, the thermocouple detects heat in one portion of the spot and not in other portions of the spot.

When organic tissue materials are heated, a gradient is typically formed with the hottest portion being in the center of the spot and coolest areas being around the spot's edges. Since the thermocouple is typically placed around the edges of the spot (to avoid obscuring the laser radiation), an accurate indication may not be provided of the temperature rise of the hottest portion of the tissue.

Another device procedure for heating with a laser is discussed in U.S. Pat. No. 4,121,087. This patent describes a technique that heats a metal reflective material with laser radiation and then senses the intensity of reflection of the laser radiation from the material. When heating tissue, the reflection characters may be modified with temperature. Therefore, when using this technique for laser welding, measuring the intensity of reflection from the tissue may result in inaccurate results.

Another device for controlling a laser is described in U.S. Pat. No. 4,316,467. This device optically senses hemangioma of skin and then regulates the laser depending on the color of the epidermis. Neither hemangioma nor color is related to tissue temperature and consequently would not be applicable when tissue welding.

A further device for laser surgery is described in U.S. Pat. No. 5,057,099. This device heats skin through an optical fiber and then monitors the heat at a radiation emitting end of the fiber. This heat on the end of the fiber may be unrelated to the final tissue temperature. As the fiber is moved, the tissue temperature changes but the temperature on the end of the fiber remains constant. Accordingly, this device would not be suited for tissue welding applications.

SUMMARY OF THE INVENTION

An object of this invention is to provide an improved method and apparatus for heating control of the temperature of material to be heated.

Another object of the invention is to heat tissue with laser radiation and maintain the tissue's final temperature within a predetermined range to allow the tissue to weld properly.

A further object is to heat tissue and maintain the tissue final temperature within a predetermined range without scorching.

An additional object is to heat tissue with laser radiation and control the intensity of the radiation by sensing black body radiation of the tissue.

Also, an object of the invention is to heat tissue with a radiation source having a first wavelength and to control the tissue's temperature by sensing a second wavelength so that the wavelength of the radiation source does not interfere with sensing the tissue temperature.

It is also an object to control the temperature of tissue when laser welding as the distance between the laser emitter and the tissue varies.

All objects at temperatures greater than absolute zero (zero degrees Kelvin) emit radiation called "black body radiation." At very low temperatures, the wavelength of these emissions is very long, i.e., in the radio frequencies. Hotter objects emit radiation at shorter wavelengths. For example, a piece of hot metal is red because it emits black body radiation at the red end of the visible spectrum.

Objects at temperatures in the vicinity of 300° Kelvin (room temperature) emit black body radiation with its strongest components in the range of 9.5 microns in wavelength (far-infrared region). The amount of power radiated by an object is a function of its temperature and is governed by the following Planck's Law:

$$W_\lambda = \frac{C_1}{\lambda^5} \times \frac{1}{e^{\frac{C_2}{\lambda \times T}} - 1}$$

where:
$W_\lambda$ = spectral radiant emittance units of Watts/cm$^2$/micron
$\lambda$ = Wavelength in microns
T = Temperature in degrees Kelvin
$C_1 = 2\Pi \times h \times C_2 = 3.7415 \times 10^4$ W cm$^{-2}\mu^4$
$C_2 = ch/k = 1.43879 \times 10^4 \mu^\circ$ K.

From Planck's Law, the black body radiation of human skin before irradiation by the laser treatment beam (at 305 degrees Kelvin) is about 3.4 milliwatts per cm$^2$ per micron in the vicinity of 9.5 microns.

The black body radiation of skin at the tissue-welding temperature of 60 degrees Celsius (333° Kelvin) is about 5.2 milliwatts per cm$^2$ per micron, an increase of 53% in emitted black body radiation power over the pre-irradiated case. The emitted black body radiation changes much more dramatically than the small temperature increase might suggest. This dramatic increase allows accurate measurements of temperature to be sensed with a fiber detector in a non-contact mode using black body radiation.

Summing the available radiation according to Planck's Law in the spectral region of from 8 to 12 microns translates into about 13 milliwatts per cm$^2$ at 305° Kelvin. For a spot area of 1.5 millimeters in diameter, the area is 0.018 cm$^2$, giving a radiant power of about 230 microwatts (greater than a 50% increase in radiation power over the unheated spot). Thus, 230 microwatts is the maximum available power for the detector to "see" from the unheated skin in a spot 1.5 mm in diameter.

However, the sense fiber does not capture all of the available power radiated from the tissue, since power is radiated into a full hemisphere, while the field of view of the fiber is a cone with a solid angle much less than a hemisphere. A single sense fiber typically captures 1% to 2% of this power. Thus, multiple sense fibers could be used to increase the ability of the system to sense the emitted radiation.

The aforementioned objects are accomplished by sensing black body radiation emitted by tissue and then controlling the laser in response to the sensed black body radiation, In the preferred embodiment of the invention an apparatus for welding with optical energy is provided. This apparatus includes a means for projecting a beam of coherent light having a welding wavelength onto a region to be welded so as to heat the region and further includes the means for detecting changes in temperature of the region by sensing variations in a characteristic black body radiation emitted by the region due to the beam heating the region. The invention also includes means for controlling the projection of the beam as a function of the detected variations of the characteristic black body radiation. Preferably, the detecting means has a field of view that is coincident with the projected beam on the surface of the region to be welded. In this way, as the operator moves the beam, the temperature of the heated region can be sensed with a great deal of accuracy to maintain an accurate end temperature.

In another aspect of the invention a method of conducting a surgical procedure with a laser is disclosed. The procedure comprises the steps of emitting a laser beam of coherent light energy having a tissue welding wavelength on a region of tissue to be heated. The characteristic black body radiation emitted by the region is changed due to the laser beam heating the region. This change is then detected. The projection of the beam is controlled as a function of the detected change in the characteristic such that the temperature of the tissue in the heated region is maintained within a predetermined range. Preferably, the laser beam wavelength is between about 1 and 1.8 microns and the black body radiation sensed is between about 8 and 12 microns in wavelength.

DESCRIPTION OF THE PREFERRED EMBODIMENT

Figure 1:
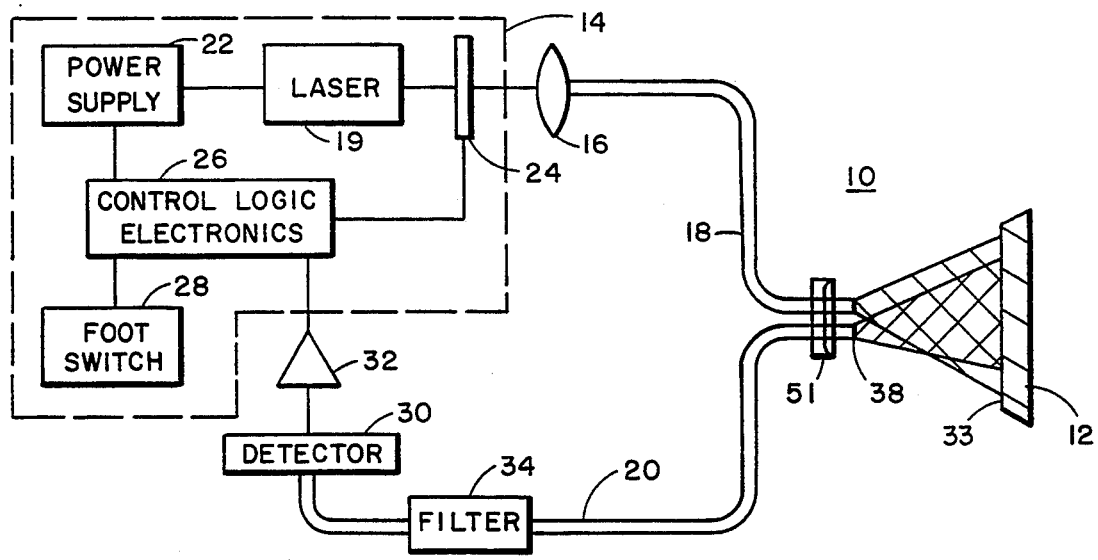
FIG. 1 is a simplified block diagram of one form of the present invention as applied to a system for heating a material.

Referring to FIG. 1, there is shown a block diagram of a system 10 for heating or welding material 12. Heating system 10 includes a laser system 14 optically coupled through a focusing lens 16 to near-infrared optical fiber 18. Coherent light passes through fiber 18 to generate a projecting beam on a surface 33 of material 12. Laser system 14 receives infrared IR wavelengths from material 12 through waveguide 20. This system 14 responds to the far infrared wavelength energy enabling-/disabling coherent energy fed through optical fiber 18 through material 12.

Preferably, the far infrared waveguide 20 is a hollow metallic waveguide, a hollow dielectric waveguide, or an optical fiber which transmits far infrared, such as a fiber of the thallium-bromoiodide (KRS-5) or chalcogenide glass. Waveguide 20 can also be a conventional lens or far infrared gradient index lens. Hollow waveguides and true fiber structures of small physical dimensions permit radiation into the vicinity of the handpiece type.

Laser system 14 includes a laser 19 which preferably generates coherent light energy in the 1.0–1.8 micron region. Laser 19 is powered by power supply 22 and has its output controlled by shutter 24. Control logic electronics 26 activates power supply 22 and shutter 24. Control logic electronics 26 is enabled by foot switch 28, also referred to as a foot pedal, and is fed black body radiation from infrared detector 30 through preamplifier 32. Infrared detector 30 is preferably coupled through an optical filter 34 to far infrared waveguide 20. Filter 34 preferably passes radiation having a wavelength between 8 and 12 microns. Focusing lens 16 is optically coupled to near infrared optical fiber 18. Fiber 18 and waveguide 20 are connected together with a hand piece 51 for controlling the action of the radiation emitter or distal end 38 of optical fiber 18 and the distal end 40 of waveguide 20. Fiber 18 and waveguide 20 are oriented in the same direction so that the field of view of waveguide 20 is coincident with the projecting beam of laser radiation on the surface 33 of material 12 from the distal end 38 of fiber 18.

During operation of the heating system 10, the surgeon depresses foot switch 28 which feeds a signal to control logic electronics 26 to open shutter 24. Shutter 24 responds to the signal from control logic electronics 26 by opening and allowing a 1.3 micron wavelength near infrared laser radiation from laser 19 to be delivered to focusing lens 16 which focuses the projecting beam from laser 19 into the proximal end of fiber 18. The coherent energy or laser light propagates the length of fiber 18 through handpiece 51 and out the distal end 38 of fiber 18. On the distal end 38 of fiber 18, the light diverges to form a beam of a circular cone shape with an incident angle of approximately 22 degrees off surface 33 of the target material 12.

When the laser light from the distal end 38 is directed at a tissue of 3 mm thick, the laser light fills a spot of approximately 1.5 mm in diameter. The 1.3 micron laser radiation is absorbed by tissue material to begin the process of heating from its initial temperature of about 32 degrees C. to a final denaturization temperature at which the protein content of the tissue forms a biological glue. In most tissue, the denaturization temperature ranges from between 45 to 60 degrees C.

The far-infrared black body radiation emitted by the tissue material 12 is detected by the far infrared optical waveguide 20 which feeds the detected radiation through optical filter 34 to the infrared detector 30. Preferably filter 34 has an optical passband in the region of 8-12 microns to pass black body radiation emitted by the tissue. Black body radiation has an intensity which is a function of temperature of material 12 in accordance with Planck's Law as previously described. Preferably, filter 34 is selected to prohibit detector 30 from responding to any of the near infrared 1.3 micron treatment beam that may be reflected from the surface of the tissue.

One preferable form of detector 30 is a quantum type, such as mercury cadmium telluride (HgCdTe) and lead tin telluride (PbSnTe). These detector materials typically operate as detectors at temperatures between 200 degrees Kelvin down to cryogenic temperatures of 77° Kelvin or lower. Cooling is employed to reduce the thermal noise of the detector itself, otherwise the detector would be at the same temperature as the material to be sensed. These devices are available to operate at room temperature and have enough sensitivity and low enough noise to be employed in a tissue welding operation.

Quantum type detectors have the advantage of being able to respond to a non-time-varying signal. This allows these quantum type detectors to "stare" continuously when an end area has been reached and respond linearly to any changes in photon flux incident on them as a result of increasing black body radiation. Thermal type detectors may be used but require a mechanical chopper between them and the photon source as these detectors respond only to a change in photon flux.

The signal level of the detector with a DC response (the "quantum" type detector) is linearly proportional to the number of photons arriving at the detectors surface and is used to gauge the black body radiation of the tissue welding spot. The far infrared fiber may be a hollow waveguide, lens train, GRIN lens or optical fiber. To improve collection efficiency of the far-infrared fiber, the transmission of the spectral filter, the detector itself and the entire assembly could be calibrated by aiming the fiber at a black body source of known temperature and recording the maximum signal from the detector. The known temperature could be used as a reference signal for tissue welding.

Other methods for determining a reference temperature are to point the sensing fiber at a reference black body source with the goal or desired end temperature of the tissue, e.g., 60° C. A small oscillating mirror could then be used to divert the beam several times per second at the sensing fiber so that the sensing fiber would periodically compare the signal from the tissue spot to the signal from the reference black body source. When the signal levels are identical, the end point temperature would be achieved. Such implementation, although more complex, would be able to continuously self-calibrate any moment-by-moment changes of the variables that can affect the signal level from the material and these signal level variables could be corrected automatically.

The output of detector 30 is fed through preamplifier 32 which magnifies the signal level of the detector 30. Preamplifier 32 then delivers the amplified signal to control electronics 26.

Figure 2:
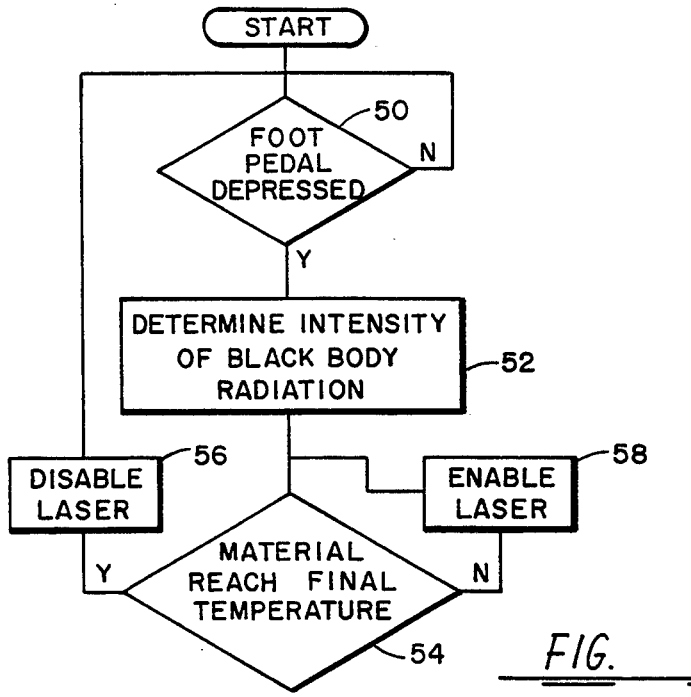
FIG. 2 is a flow diagram of a process executed by the control logic electronics shown in FIG. 1.

Control electronics 26 includes a processor (not shown) which executes modules 52-58 (FIG. 2). The processor in control electronics 26 determines in module 50 when the foot switch 28 is depressed. When the foot switch 28 is depressed, the processor executes module 52. Until the foot switch 28 is depressed, the processor continues to execute module 50.

In module 52, logic electronics 26 determines the value of the intensity of far-infrared wavelength radiation from preamplifier 32 corresponding to the black body radiation on surface 33 of material 12. The processor then executes module 54.

In module 54, the processor compares the value of the signal from preamplifier 32 to a reference value corresponding to a level at which material 12 reaches its final desired goal temperature. In the case of tissue, this temperature is between about 45 and 60 degrees C. When this value has been reached, electronics 26 executes module 56. If this temperature has not been reached, electronics 26 executes module 58. In module 56, electronics 26 disables the laser 19 by either shutting shutter 24 to terminate the exposure or disabling power supply 22.

If the temperature of the tissue material is less than the reference temperature, in module 58, the shutter 24 remains open and laser 19 is enabled. After executing module 58, module 54 and 58 continue to be executed until the sensed temperature reaches the desired end point.

After executing module 56, control electronics 26 executes module 50 and subsequently modules 52-58 to heat subsequent areas or regions of the material 12 in a similar manner. Although the system is shown to be configured to respond to subsequent depressions of the foot switch 28 to initiate the action, the system 10 can be easily modified to incorporate a considerable rest period for the operator to advance the handpiece to the next tissue welding or heating location before reopening shutter 24 to continue the process.

An alternative to controlling the shutter 24 in modules 56 and 58 is to trigger modules 56 and 58 to disable and enable power supply 22. By disabling the power supply 22, the laser light from laser 14 may be directly enabled by turning on the drive currents at the beginning of the heating process and similarly disabling at the conclusion of the process.

Critical to this method of heating, the field of views of the distal ends of the near infrared optical fibers 18 and optical waveguide 20 are coincident on surface 42 of material 12. The black body radiation detected by far-infrared waveguide 20 must come from the same spot where the treatment beam is absorbed by the material 12.

In an alternate embodiment, the system 20 permits continuous motion heating or tissue welding. In this method, the radiating beam need not be held stationary until the conclusion of the welding or heating operation before being advanced to the next spot. In continuous motion heating, the beam may be continuously advanced on an approximated margin area or region to be welded. With this method, the intensity of the beam will be varied in proportion to the velocity of the advance to maintain the heated region at the desired welding temperature.

Referring to FIG. 2, in the continuous welding implementation of module 54, the processor within control logic electronics 26 determines the difference between a reference value prestored in the control logic and the value of the far-infrared intensity signal from preamplifier 32. In this implementation, logic electronics 26 does not execute module 58, and in module 56 power supply 22 is adjusted to vary the output of laser 14. Laser 14 output is set to be a function of the difference between the reference value stored in the control logic and the value fed to logic electronics 26 from preamplifier 32.

For example, if the operator holds the distal end of fiber 18 in a stable location, the laser exposure will begin and the material 12, such as tissue, will be heated. The detector 30 begins to measure the black body radiation indicative of the temperature, as the temperature begins to rise, from approximately 32 degrees C. of normal skin temperature towards a tissue welding temperature of between about 45 and 60 degrees C. As the signal from preamplifier 32 approaches the reference value at the thermal end point, the power supply level is decreased to lower the laser output proportional to the difference between the measured value and the reference point. If the laser beam exiting the distal end 38 of fiber 18 continues to the same point on material 12, laser 19 output will be decreased to a point where the power delivered to the irradiated spot would just offset the steady state heat loss associated with convection and conduction of radiation. Thus, the temperature of the spot will be maintained at a set reference value level.

If, for example, the handpiece 51 is moved such that the spot follows the line of the an approximated lesion or wound, the far-infrared black body radiation sensed by detector 30 via feedback waveguide 20 would decrease. The processor in modules 54 and 56 compares the signal level from the detector 30 to the reference value. The control electronics 26 then responds by feeding a signal to laser power supply 22 to increase power delivered to the laser 19. The laser 19 then responds to the increase by increasing the amount of 1.3 micron laser power delivered to tissue welding and the temperature of the tissue rises rapidly towards the reference value. The magnitude of the increase in the laser power output is proportional to the difference between the measured tissue temperature indicated by the magnitude of the far-infrared black body radiation and the reference value which represents the optimum tissue welding temperature.

It is recognized by this method that the laser power delivered to the tissue or material 12 will be related to the velocity at which the spot moves. In this manner, the continuous motion system will compensate for variations in spot size as well as changes in velocity of the handpiece along the incision line of the lesion.

Figure 3:
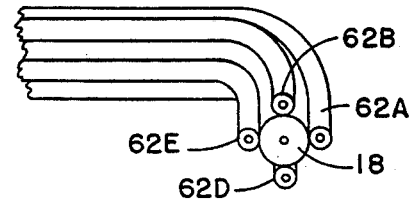
FIG. 3 is an end view of a multiple waveguide implementation of the far infrared waveguide shown in FIG. 1.
Figure 4:
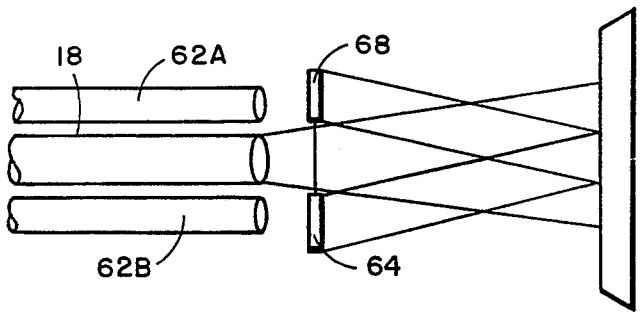
FIG. 4 is a side view of a far-infrared fiber and a toroidal lens replacing the waveguide shown in FIG. 1.

Referring to FIGS. 3 and 4, there are shown alternate embodiments of the invention using a waveguide detector. Referring to FIG. 1, a waveguide 20 may be hollow and positioned adjacent to the treatment fiber 18. Preferably the distal end of waveguide 20 is angled such that the field of view of the feedback waveguide 20 coincides with the treatment beam from fiber 18 at the surface 42 of material 12.

Referring to FIG. 3, waveguide 20 may comprise a plurality of waveguides or fibers arrayed about fiber 18 so as to increase the collection efficiency of the black body radiation from which the tissue temperatures will be measured. These feedback fibers may have their upper ends combined to impinge on a single detector 30 to enhance both the amplitude of a signal level and the signal to noise ratio of the system. Alternatively, each feedback fiber 62A–62D may be coupled to an individual detector 30 and the electrical output of the detectors summed. The ends of these fibers 62A–62D may be angled with a prism to have the same field of view. Further, these fiber ends may be angled and polished to eliminate the need for a prism.

Referring to FIG. 4, another alternate implementation is shown where toroidal lens 64 is placed at the end of the feedback fiber array so that the lens has the same affect as individually dressing the ends of the fibers at an angle. The object in this embodiment, with the combination of toroidal lens 64 optically coupling fibers 62A–62D is to make the field of view of the fibers 62A–62D coincident with the field of view of the treatment projected from within optical fiber 18. By making the field of view coincident, tissue temperature information from the heated welding location becomes more accurate.

This concludes the description of the preferred embodiments. A reading by those skilled in the art will bring to mind various changes without departing from the spirit and scope of the invention. It is intended, however, that the invention only be limited by the following appended claims.

What is claimed is:

1. An apparatus for heating tissue comprising:
   means for projecting a beam of optical radiation energy having a first wavelength on a surface of a region to be welded so as to heat the region;
   means for detecting changes in temperature of the region by sensing variations of a characteristic of black body radiation emitted by the region due to the beam heating the region, said black body radiation having a wavelength different from the first wavelength; and
   means for controlling the projection of the beam as a function of the detected variations of the characteristic.

2. The apparatus as recited in claim 1 further comprising means for moving the beam relative to the region being heated.

3. The apparatus as recited in claim 1 further comprising a passband filter operatively coupled to the detecting means and operative to limit the detected black body radiation wavelength to wavelengths outside the welding wavelength.

4. The apparatus as recited in claim 1 wherein the projecting means projects a first wavelength within the range of about 1 to 1.8 microns and wherein the detecting means senses black body radiation wavelengths between about 8 to 12 microns.

5. The apparatus as recited in claim 1 wherein the detecting means has a field of view that is coincident with the projected beam on the surface of the region to be welded.

6. A method of conducting a surgical procedure with optical radiation comprising the steps of:
projecting a beam of optical radiation having a tissue welding wavelength on a region of tissue to be welded;
detecting changes in a characteristic of black body radiation emitted by the region due to the beam of optical radiation heating the region;
controlling the projection of the beam as a function of the detected changes in the characteristic; and
maintaining the temperature of the tissue in the heated region within a predetermined range.

7. The method as recited in claim 6 wherein the emitted black body radiation has a wavelength between about 8 and 12 microns and further comprising the step of maintaining the tissue welding wavelength at a different wavelength than the black body radiation wavelength.

8. The method as recited in claim 6 further comprising the step of maintaining a characteristic wavelength of the black body radiation between about 8 and 12 microns.

9. The method as recited in claim 6 further comprising the step of moving the beam relative to the region being heated.

10. The method as recited in claim 6 further comprising the step of varying the intensity of the projected beam on the region as a function of the velocity at which the beam is moved.

11. The method as recited in claim 6 further comprising the steps of:
raising the temperature of the region of the tissue when the beach is projected; and
limiting the temperature of the region to a maximum amount when controlling the projection.

12. The method as recited in claim 6 further comprising the steps of:
providing a black body radiation reference value corresponding to an optimum maximum temperature of the tissue region; and
controlling intensity of the optical radiation wavelength as a function of the difference between the detected characteristic and the reference value.

13. The method as recited in claim 12 wherein the characteristic comprises a signal representative of the radiated energy from the tissue and the step of controlling includes the step of adjusting the optical radiation intensity so that the radiated energy corresponds to the optimum maximum temperature of the region.

14. The method as recited in claim 6 further comprising the step of maintaining a field of view when detecting changes in the characteristic that is coincident with the projecting beam on the surface of the region to be welded.

15. The method as recited in claim 6 further comprising the step of maintaining the wavelength of the tissue welding beam between about 1 and 1.8 microns.

16. An apparatus for heating tissue with optical radiation comprising:
a laser device operative to project a beam of coherent light having a tissue welding wavelength on a surface of a tissue to be welded so as to heat the tissue, said device having a movable end from which coherent light is emitted onto the surface of the tissue;
a sensor means connected to the laser device adjacent to the moveable end for sensing changes in the temperature of the surface of the tissue by detecting variations in amplitude of black body radiation emitted by the surface of the tissue, said sensor means having a field of view that is coincident with the projecting beam on the surface of the tissue being heated; and
a control circuit means for adjusting the intensity of the beam of coherent light as a function of the variation in the amplitude of the black body radiation detected by the sensor means.

17. The apparatus as recited in claim 16 wherein said welding wavelength of said laser device is between 1 and 1.8 microns and wherein the sensor means detects variations the black body radiation wavelength is between 8 and 12 microns.

18. The apparatus as recited in claim 16 wherein the control circuit means reduces the intensity of the beam when the amplitude of the detected black body radiation approaches a predetermined reference value.

19. The apparatus as recited in claim 18 wherein the control circuit means reduces the intensity of the beam when the detected wavelength approaches a predetermined reference value corresponding to the temperature at which the tissue shrinks when heated.

20. The apparatus as recited in claim 16 further comprising means for moving the sensor means relative to the tissue.

21. The apparatus as recited in claim 16 wherein the black body radiation has a wavelength different than the welding wavelength emitted by the laser device.

22. The apparatus as recited in claim 16 further comprising a pass band filter means operatively coupled to the sensor for limiting the wavelength sensed by the sensor means to between about 8 and 12 microns.

23. The apparatus as recited in claim 16 wherein the laser device projects the beam through a near infrared fiber.

24. The apparatus as recited in claim 16 wherein the sensor means includes an optical waveguide through which the black body radiation is detected.

25. The apparatus as recited in claim 24 wherein the optical waveguide is constructed of a thallium-bromo-iodide material.

* * * * *